United States Patent
Hentsch et al.

(12) 
(10) Patent No.: US 7,166,701 B2
(45) Date of Patent: Jan. 23, 2007

(54) HUMAN SURVIVIN INTERACTING PROTEIN 1 (SIP-1)

(75) Inventors: Bernd Hentsch, Darmstadt (DE); Klaus Dücker, Darmstadt (DE); Björn Hock, Maintal (DE)

(73) Assignee: Merck Patent GmbH, Darmstadt (DE)

( * ) Notice: Subject to any disclaimer, the term of this patent is extended or adjusted under 35 U.S.C. 154(b) by 531 days.

(21) Appl. No.: 10/239,391

(22) PCT Filed: Mar. 21, 2001

(86) PCT No.: PCT/EP01/03204

§ 371 (c)(1),
(2), (4) Date: Sep. 24, 2002

(87) PCT Pub. No.: WO01/73014

PCT Pub. Date: Oct. 4, 2001

(65) Prior Publication Data

US 2004/0254346 A1 Dec. 16, 2004

(30) Foreign Application Priority Data

Mar. 24, 2000 (EP) .......................................... 001064088

(51) Int. Cl.
*C07K 1/00* (2006.01)
*C07K 14/00* (2006.01)
*C07K 16/00* (2006.01)
*C12P 21/06* (2006.01)
*G01N 33/53* (2006.01)

(52) U.S. Cl. ..................... 530/350; 435/69.1; 435/7.1; 536/23.1; 536/23.4; 530/387.1

(58) Field of Classification Search ................ 435/69.1, 435/7.1; 530/350, 387; 536/23.1–23.4
See application file for complete search history.

(56) References Cited

FOREIGN PATENT DOCUMENTS

WO    WO 00/58473    *   8/2000

OTHER PUBLICATIONS

Bloecker H., Boecher M., Brandt P., Mewes H.W., Gassenhuber J., Wiemann S. 1999 cDNA DKFZp434O0515, Homo sapiens mRNA, EMBL/GenBank/DDBJ databases.*

Database EMBL, Heidelberg, FRG. (Online): Oct. 20, 1999: "Homo sapiens mRNA"; AA306831 XP002174515.

* cited by examiner

*Primary Examiner*—Karen Cochrane Carlson
*Assistant Examiner*—Marsha Tsay
(74) *Attorney, Agent, or Firm*—Millen, White, Zelan & Branigan

(57) ABSTRACT

Survivin Interacting Protein 1 and polynucleotides and methods for producing such polypeptides by recombinant techniques are disclosed. Also disclosed are methods for utilizing SIP-1 polypeptides and polynucleotides in diagnostic assays.

13 Claims, 4 Drawing Sheets

HUMAN SURVIVIN INTERACTING PROTEIN 1 (SIP-1)

FIELD OF THE INVENTION

Figure 1:
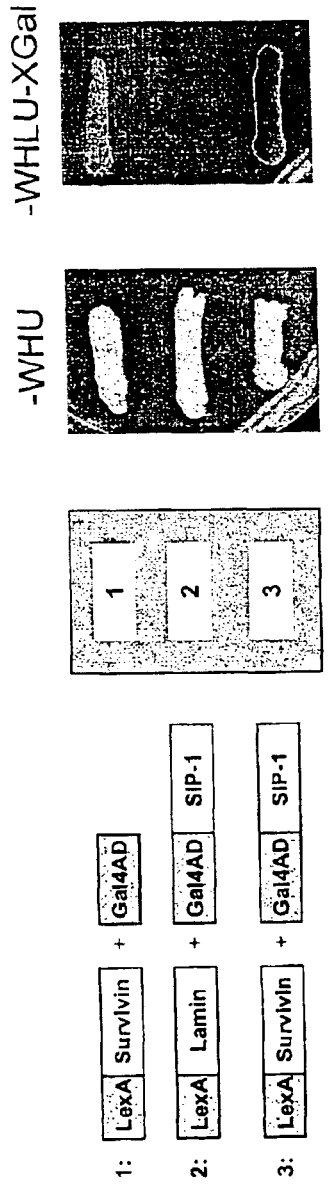
Figure 2:
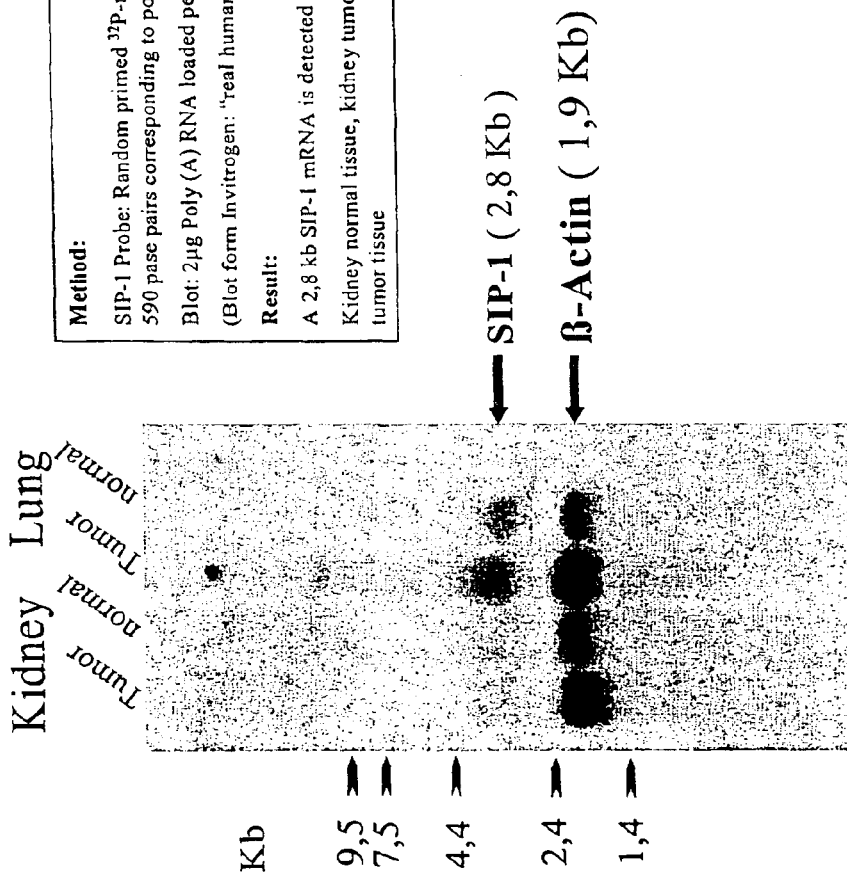
Figure 3:
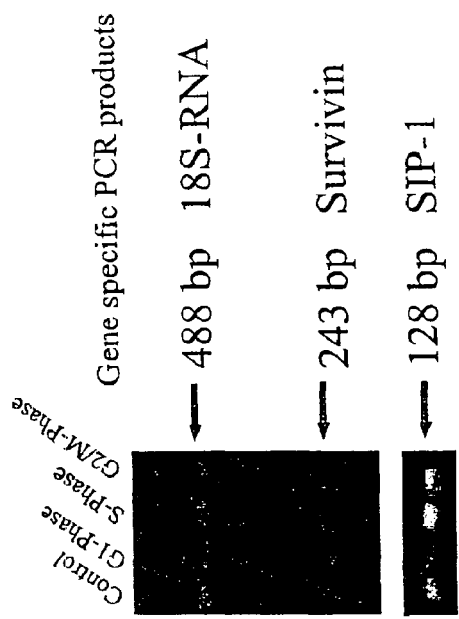
Figure 4:
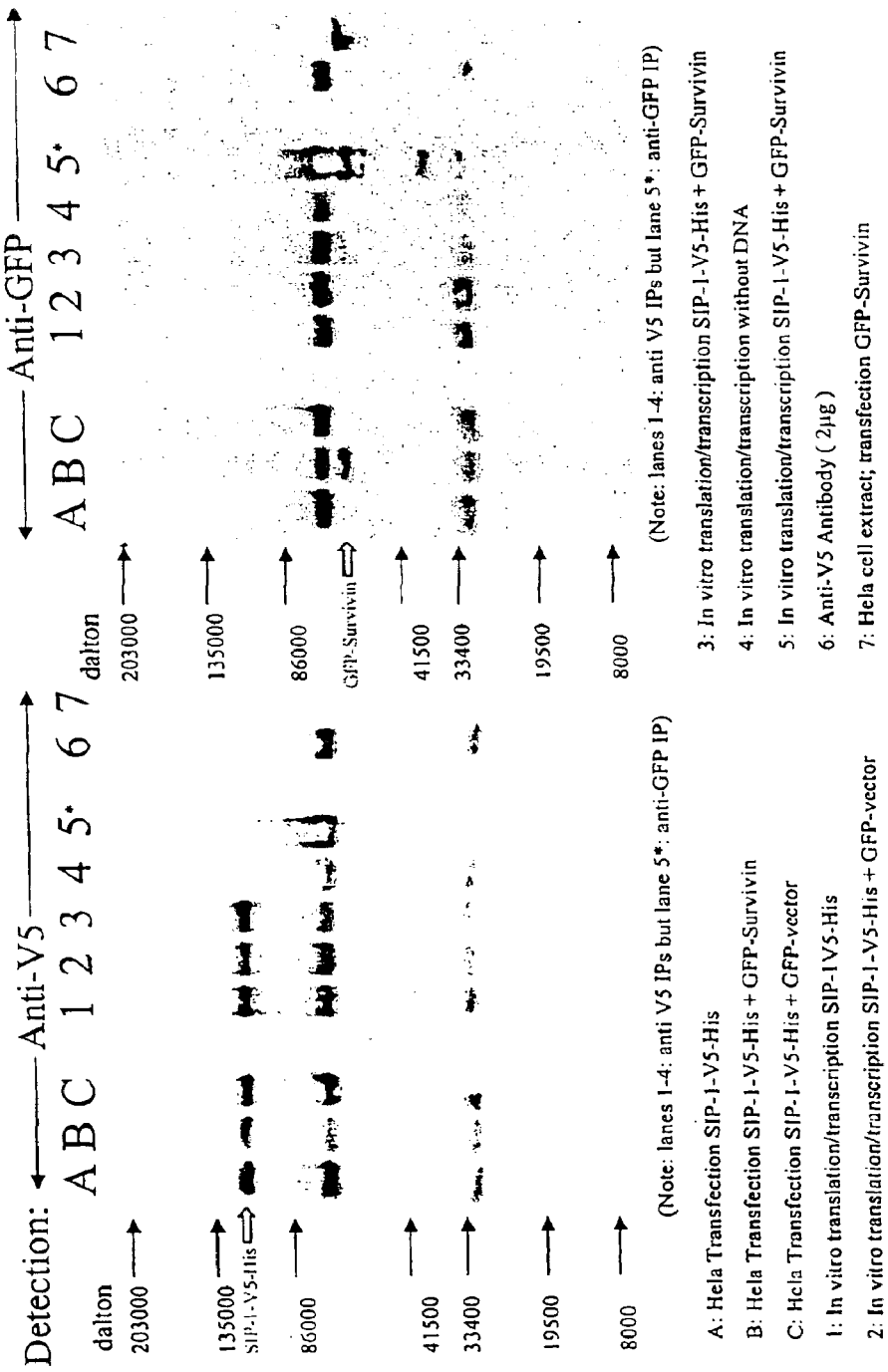

This invention relates to newly identified polypeptides and polynucleotides encoding such polypeptides sometimes hereinafter referred to as *Survivin* Interacting Protein 1 or "SIP-1", to their use in diagnosis and in identifying compounds that may be agonists, antagonists that are potentially useful in therapy, and to production of such polypeptides and polynucleotides.

BACKGROUND OF THE INVENTION

The drug discovery process is currently undergoing a fundamental revolution as it embraces "functional genomics", that is, high throughput genome- or gene-based biology. This approach as a means to identify genes and gene products as therapeutic targets is rapidly superseding earlier approaches based on "positional cloning". A phenotype, that is a biological function or genetic disease, would be identified and this would then be tracked back to the responsible gene, based on its genetic map position.

Functional genomics relies heavily on high-throughput DNA sequencing technologies and the various tools of bioinformatics to identify gene sequences of potential interest from the many molecular biology databases now available. There is a continuing need to identify and characterise further genes and their related polypeptides/proteins, as targets for drug discovery. Recent advances in this area are mainly driven by applying advanced screening systems with focus to the function of newly identified proteins. Interesting application for this type of screens are whithin the field of tumor apoptosis.

Apoptosis of tumor cells can be blocked e.g. by mutations in crucial genes like those frequently found in the well known p53 tumor suppressor protein. Another mechanism that blocks apoptosis is caused by the protein family of "inhibitors of apoptosis" (IAPs), reviewed by Deveraux and Reed (Genes & Development 1999). One member of this family is encoded by the Survivin gene.

The strongest evidence for an IAP involvement in cancer is seen for *Survivin* (see review of Altieri and Marchisio, Laboratory Investigation 1999). Although not observed in adult differentiated tissue, *Survivin* becomes prominently expressed in transformed cell lines and in all of the most common human cancers of lung, colon, pancreas, prostate and breast, in vivo. Survivin is also found in approximately 50% of high-grade non-Hodgkin's lymphomas (centroblastic, immunoblastic), but not in low-grade lymphomas (lymphocytic). Survivin inhibits caspase activity and apoptosis induced by Fas (CD95), Bax, Caspases, and anti-cancer drugs.

In addition, Survivin is upregulated 40-fold at G2/M phase of the cell cycle and binds to mitotic spindles (microtubules), although its role at the spindle is still unclear. There might be a connected control of apoptosis and mitotic spindle checkpoint by *Survivin*. Disruption of *Survivin*-microtubule interactions results in loss of *Survivin's* anti-apoptosis function and increased caspase-3 activity. *Survivin* may counteract a default induction of apoptosis in G2/M phase. The overexpression of *Survivin* in cancer may overcome this apoptotic checkpoint and favour aberrant progression of transformed cells through mitosis (Fengzhi et al., Nature 1998). In this repect it is important to note that it was recently shown that *Survivin* initiates procaspase 3/p21 complex formation as a result of interaction with Cdk4 to resist Fas-mediated cell death (Suzuki et al., Oncogene 2000). SIP-1 may therefore be implicated in the known tumor-cell-escape from the immune system. The other biochemical mechanisms, besides its inhibitory binding to Caspases, by which *Survivin* might mediate its anti-apoptotic activity are currently unclear.

Therefore in this invention we have screened for potential ligands that interact with *Survivin*.

SUMMARY OF THE INVENTION

The present invention relates to *Survivin* Interacting Protein 1 (*GENE NAME), in particular *GENE NAME polypeptides and *GENE NAME polynucleotides, recombinant materials and methods for their production. Such polypeptides and polynucleotides are of interest in relation to methods of treatment of certain diseases, because they are natural ligands for *Survivin*. As pointed out this molecule has a prominent role in anti-apoptotic activity.

*Survivin* becomes prominently expressed in most common human cancers of lung, liver, colon, stomach, skin, pancreas, prostate, ovary and breast, in vivo. *Survivin* is also found in approximately 50% of high-grade non-Hodgkin's lymphomas thus the interaction with the newly described molecule of this invention SIP-1 offers an attractive option to interfere with this diseases therefore they are hereinafter referred to as "diseases of the invention". In a further aspect, the invention relates to methods for identifying agonists and antagonists (e.g., inhibitors) using the materials provided by the invention, and treating conditions associated with *GENE NAME activity with the identified compounds. In a still further aspect, the invention relates to diagnostic assays for detecting diseases associated with inappropriate *GENE NAME activity or levels.

DESCRIPTION OF THE INVENTION

In a first aspect, the present invention relates to *GENE NAME polypeptides. Such polypeptides include:

(a) a polypeptide encoded by a polynucleotide comprising the sequence of SEQ ID NO:1;

(b) an polypeptide comprising a polypeptide sequence having at least 95%, 96%, 97%, 98%, or 99% identity to the polypeptide sequence of SEQ ID NO:2;

(c) a polypeptide comprising the polypeptide sequence of SEQ ID NO:2;

(d) a polypeptide having at least 95%, 96%, 97%, 98%, or 99% identity to the polypeptide sequence of SEQ ID NO:2;

(e) the polypeptide sequence of SEQ ID NO:2; and (f) a polypeptide having or comprising a polypeptide sequence that has an Identity Index of 0.95, 0.96, 0.97, 0.98, or 0.99 compared to the polypeptide sequence of SEQ ID NO:2;

(g) fragments and variants of such polypeptides in (a) to (f).

Polypeptides of the present invention are believed to represent ligands for *Survivin* and thus may counteract a default induction of apoptosis. Furthermore *Survivin* and its ligand SIP-1 may control apoptotic checkpoint and SIP-1 may be a mediator of *Survivin's* anti-apoptotic activity.

SIP-1 polypeptides may be involved in the establishment of a *survival* signal of tumor cells which may result in resistance of these cells against apoptotic signals, e.g. chemotherapeutic agents or physiological death signals as such of immune cells.

The biological properties of the *GENE NAME are hereinafter referred to as "biological activity of *GENE NAME" or "*GENE NAME activity". Preferably, a polypeptide of the present invention exhibits at least one biological activity of *GENE NAME.

Polypeptides of the present invention also includes variants of the aforementioned polypeptides, including all allelic forms and splice variants. Such polypeptides vary from the reference polypeptide by insertions, deletions, and substitutions that may be conservative or non-conservative, or any combination thereof. Particularly preferred variants are those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination.

Preferred fragments of polypeptides of the present invention include a polypeptide comprising an amino acid sequence having at least 30, 50 or 100 contiguous amino acids from the amino acid sequence of SEQ ID NO: 2, or a polypeptide comprising an amino acid sequence having at least 30, 50 or 100 contiguous amino acids truncated or deleted from the amino acid sequence of SEQ ID NO: 2. Preferred fragments are biologically active fragments that mediate the biological activity of *GENE NAME, including those with a similar activity or an improved activity, or with a decreased undesirable activity. Also preferred are those fragments that are antigenic or immunogenic in an animal, especially in a human.

Fragments of the polypeptides of the invention may be employed for producing the corresponding full-length polypeptide by peptide synthesis; therefore, these variants may be employed as intermediates for producing the full-length polypeptides of the invention. The polypeptides of the present invention may be in the form of the "mature" protein or may be a part of a larger protein such as a precursor or a fusion protein. It is often advantageous to include an additional amino acid sequence that contains secretory or leader sequences, pro-sequences, sequences that aid in purification, for instance multiple histidine residues, or an additional sequence for stability during recombinant production.

Polypeptides of the present invention can be prepared in any suitable manner, for instance by isolation form naturally occurring sources, from genetically engineered host cells comprising expression systems (vide infra) or by chemical synthesis, using for instance automated peptide synthesizers, or a combination of such methods. Means for preparing such polypeptides are well understood in the art.

In a further aspect, the present invention relates to *GENE NAME polynucleotides. Such polynucleotides include:

(a) a polynucleotide comprising a polynucleotide sequence having at least 95%, 96%, 97%, 98%, or 99% identity to the polynucleotide sequence of SEQ ID NO:1;

(b) a polynucleotide comprising the polynucleotide of SEQ ID NO:1;

(c) a polynucleotide having at least 95%, 96%, 97%, 98%, or 99% identity to the polynucleotide of SEQ ID NO:1;

(d) the polynucleotide of SEQ ID NO:1;

(e) a polynucleotide comprising a polynucleotide sequence encoding a polypeptide sequence having at least 95%, 96%, 97%, 98%, or 99% identity to the polypeptide sequence of SEQ ID NO:2;

(f) a polynucleotide comprising a polynucleotide sequence encoding the polypeptide of SEQ ID NO:2;

(g) a polynucleotide having a polynucleotide sequence encoding a polypeptide sequence having at least 95%, 96%, 97%, 98%, or 99% identity to the polypeptide sequence of SEQ ID NO:2;

(h) a polynucleotide encoding the polypeptide of SEQ ID NO:2;

(i) a polynucleotide having or comprising a polynucleotide sequence that has an Identity Index of 0.95, 0.96, 0.97, 0.98, or 0.99 compared to the polynucleotide sequence of SEQ ID NO:1;

(j) a polynucleotide having or comprising a polynucleotide sequence encoding a polypeptide sequence that has an Identity Index of 0.95, 0.96, 0.97, 0.98, or 0.99 compared to the polypeptide sequence of SEQ ID NO:2; and polynucleotides that are fragments and variants of the above mentioned polynucleotides or that are complementary to above mentioned polynucleotides, over the entire length thereof.

Preferred fragments of polynucleotides of the present invention include a polynucleotide comprising an nucleotide sequence having at least 15, 30, 50 or 100 contiguous nucleotides from the sequence of SEQ ID NO: 1, or a polynucleotide comprising an sequence having at least 30, 50 or 100 contiguous nucleotides truncated or deleted from the sequence of SEQ ID NO: 1.

Preferred variants of polynucleotides of the present invention include splice variants, allelic variants, and polymorphisms, including polynucleotides having one or more single nucleotide polymorphisms (SNPs).

Polynucleotides of the present invention also include polynucleotides encoding polypeptide variants that comprise the amino acid sequence of SEQ ID NO:2 and in which several, for instance from 50 to 30, from 30 to 20, from 20 to 10, from 10 to 5, from 5 to 3, from 3 to 2, from 2 to 1 or 1 amino acid residues are substituted, deleted or added, in any combination.

In a further aspect, the present invention provides polynucleotides that are RNA transcripts of the DNA sequences of the present invention. Accordingly, there is provided an RNA polynucleotide that:

(a) comprises an RNA transcript of the DNA sequence encoding the polypeptide of SEQ ID NO:2;

(b) is the RNA transcript of the DNA sequence encoding the polypeptide of SEQ ID NO:2;

(c) comprises an RNA transcript of the DNA sequence of SEQ ID NO:1; or (d) is the RNA transcript of the DNA sequence of SEQ ID NO:1;

and RNA polynucleotides that are complementary thereto.

The polynucleotide sequence of SEQ ID NO:1 is a cDNA sequence that encodes the polypeptide of SEQ ID NO:2. The polynucleotide sequence encoding the polypeptide of SEQ ID NO:2 may be identical to the polypeptide encoding sequence of SEQ ID NO:1 or it may be a sequence other than SEQ ID NO:1, which, as a result of the redundancy (degeneracy) of the genetic code, also encodes the polypeptide of SEQ ID NO:2. The polypeptide of the SEQ ID NO:2 is related to other proteins of the family of guanine exchange factors (GEFs), having homology and/or structural similarity with Homo sapiens Duo mRNA, which encodes a spectrin-like domain, coiled coil, guanosine exchange factor domain and pleckstrin homology domain [Colomer, V., Engelender, S., Sharp, A. H., Duan, K., Cooper, J. K., Lanahan, A., Lyford, G., Worley, P. and Ross, C. A.: Huntingtin-associated protein 1 binds to a Trio-like polypeptide, with a rac1 guanine nucleotide exchange factor domain. Hum. Mol. Genet. 6 (9), 1519–1525 (1997)] and to Homo sapiens Trio mRNA which displays similarities to protein kinase, rac guanine exchange factor, rho guanine exchange factor and spectrin-like repeats [Debant, A., Serra-Pages, C., Seipel, K., O'Brien, S., Tang, M., Park, S. H. and Streuli, M.: The multidomain protein Trio binds the LAR transmembrane tyrosine phosphatase, contains a protein kinase domain, and has separate rac-specific and rho-specific guanine nucleotide exchange factor domains. Proc. Natl. Acad. Sci. U.S.A. 93 (11), 5466–5471, (1996)].

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one *GENE NAME activity.

Polynucleotides of the present invention may be obtained using standard cloning and screening techniques from a cDNA library derived from mRNA of human HeLa cells (ATCC: CCL-2) and in a cDNA library derived from human fetal brain tissue (see for instance, Sambrook et al., Molecular Cloning: A Laboratory Manual, 2nd Ed., Cold Spring Harbor Laboratory Press, Cold Spring Harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro-protein sequence, or other fusion peptide portions. For example, a marker sequence that facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Polynucleotides that are identical, or have sufficient identity to a polynucleotide sequence of SEQ ID NO:1, may be used as hybridization probes for cDNA and genomic DNA or as primers for a nucleic acid amplification reaction (for instance, PCR). Such probes and primers may be used to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1, typically at least 95% identity. Preferred probes and primers will generally comprise at least 15 nucleotides, preferably, at least 30 nucleotides and may have at least 50, if not at least 100 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process comprising the steps of screening a library under stringent hybridization conditions with a labeled probe having the sequence of SEQ ID NO: 1 or a fragment thereof, preferably of at least 15 nucleotides; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 microgram/ml denatured, sheared salmon sperm DNA; followed by washing the filters in 0.1×SSC at about 65° C. Thus the present invention also includes polynucleotides, preferably with a nucleotide sequence of at least 100, obtained by screening a library under stringent hybridization conditions with a labeled probe having the sequence of SEQ ID NO:1 or a fragment thereof, preferably of at least 15 nucleotides.

The skilled artisan will appreciate that, in many cases, an isolated cDNA sequence will be incomplete, in that the region coding for the polypeptide does not extend all the way through to the 5' terminus. This is a consequence of reverse transcriptase, an enzyme with inherently low "processivity" (a measure of the ability of the enzyme to remain attached to the template during the polymerisation reaction), failing to complete a DNA copy of the mRNA template during first strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., Proc Nat Acad Sci USA 85, 8998–9002, 1988). Recent modifications of the technique, exemplified by the Marathon (trade mark) technology (Clontech Laboratories Inc.) for example, have significantly simplified the search for longer cDNAs. In the Marathon (trade mark) technology, cDNAs have been prepared from mRNA extracted from a chosen tissue and an 'adaptor' sequence ligated onto each end. Nucleic acid amplification (PCR) is then carried out to amplify the "missing" 5' end of the cDNA using a combination of gene specific and adaptor specific oligonucleotide primers. The PCR reaction is then repeated using 'nested' primers, that is, primers designed to anneal within the amplified product (typically an adapter specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems comprising a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Polynucleotides may be introduced into host cells by methods described in many standard laboratory manuals, such as Davis et al., Basic Methods in Molecular Biology (1986)

and Sambrook et al.(ibid). Preferred methods of introducing polynucleotides into host cells include, for instance, calcium phosphate transfection, DEAE-dextran mediated transfection, transvection, micro-injection, cationic lipid-mediated transfection, electroporation, transduction, scrape loading, ballistic introduction or infection.

Representative examples of appropriate hosts include bacterial cells, such as *Streptococci, Staphylococci, E. Coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector that is able to maintain, propagate or express a polynucleotide to produce a polypeptide in a host may be used. The appropriate polynucleotide sequence may be inserted into an expression system by any of a variety of well-known and routine techniques, such as, for example, those set forth in Sambrook et al., (ibid). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and/or purification.

Polynucleotides of the present invention may be used as diagnostic reagents, through detecting mutations in the associated gene. Detection of a mutated form of the gene characterized by the polynucleotide of SEQ ID NO:1 in the cDNA or genomic sequence and which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques well known in the art.

Nucleic acids for diagnosis may be obtained from a subject's cells, such as from blood, urine, saliva, tissue biopsy or autopsy material. The genomic DNA may be used directly for detection or it may be amplified enzymatically by using PCR, preferably RT-PCR, or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled *GENE NAME nucleotide sequences. Perfectly matched sequences can be distinguished from mismatched duplexes by RNase digestion or by differences in melting temperatures. DNA sequence difference may also be detected by alterations in the electrophoretic mobility of DNA fragments in gels, with or without denaturing agents, or by direct DNA sequencing (see, for instance, Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397–4401).

An array of oligonucleotides probes comprising *GENE NAME polynucleotide sequence or fragments thereof can be constructed to conduct efficient screening of e.g., genetic mutations. Such arrays are preferably high density arrays or grids. Array technology methods are well known and have general applicability and can be used to address a variety of questions in molecular genetics including gene expression, genetic linkage, and genetic variability, see, for example, M. Chee et al., Science, 274, 610–613 (1996) and other references cited therein.

Detection of abnormally decreased or increased levels of polypeptide or mRNA expression may also be used for diagnosing or determining susceptibility of a subject to a disease of the invention. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radio-immunoassays, competitive-binding assays, Western Blot analysis and ELISA assays.

Thus in another aspect, the present invention relates to a diagnostic kit comprising:

(a) a polynucleotide of the present invention, preferably the nucleotide sequence of SEQ ID NO: 1, or a fragment or an RNA transcript thereof;

(b) a nucleotide sequence complementary to that of (a);

(c) a polypeptide of the present invention, preferably the polypeptide of SEQ ID NO:2 or a fragment thereof; or (d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or susceptibility to a disease, particularly diseases of the invention, amongst others.

The polynucleotide sequences of the present invention are valuable for chromosome localisation studies. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data.

Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (co-inheritance of physically adjacent genes). Precise human chromosomal localisations for a genomic sequence (gene fragment etc.) can be determined using Radiation Hybrid (RH) Mapping (Walter, M. Spillett, D., Thomas, P., Weissenbach, J., and Goodfellow, P., (1994) A method for constructing radiation hybrid maps of whole genomes, Nature Genetics 7, 22–28). A number of RH panels are available from Research Genetics (Huntsville, Ala., USA) e.g. the GeneBridge4 RH panel (Hum Mol Genet March 1996; 5(3):339–46 A radiation hybrid map of the human genome. Gyapay G, Schmitt K, Fizames C, Jones H, Vega-Czarny N, Spillett D, Muselet D, Prud'Homme J F, Dib C, Auffray C, Morissette J, Weissenbach J, Goodfellow P N). To determine the chromosomal location of a gene using this panel, 93 PCRs are performed using primers designed from the gene of interest on RH DNAs. Each of these DNAs contains random human genomic fragments maintained in a hamster background (human/hamster hybrid cell lines). These PCRs result in 93 scores indicating the presence or absence of the PCR product of the gene of interest. These scores are compared with scores created using PCR products from genomic sequences of known location. This comparison is conducted at http://www.genome.wi.mit.edu/. The gene of the present invention maps to human chromosome Chr. 2 (D2S335–D2S2257).

The polynucleotide sequences of the present invention are also valuable tools for tissue expression studies. Such studies allow the determination of expression patterns of polynucleotides of the present invention which may give an indication as to the expression patterns of the encoded polypeptides in tissues, by detecting the mRNAs that encode them. The techniques used are well known in the art and include in situ hybridization techniques to clones arrayed on a grid, such as cDNA microarray hybridization (Schena et al, Science, 270, 467–470, 1995 and Shalon et al, Genome Res, 6, 639–645, 1996) and nucleotide amplification techniques such as PCR. A preferred method uses the TAQMAN (Trade mark) technology available from Perkin Elmer. Results from these studies can provide an indication of the normal function of the polypeptide in the organism. In addition, comparative studies of the normal expression pattern of mRNAs with that of mRNAs encoded by an alternative form of the same gene (for example, one having an alteration in polypeptide coding potential or a regulatory mutation) can provide valuable insights into the role of the polypeptides of the present invention, or that of inappropriate expression thereof in disease. Such inappropriate expression may be of a temporal, spatial or simply quantitative nature.

A further aspect of the present invention relates to antibodies. The polypeptides of the invention or their fragments, or cells expressing them, can be used as immunogens to produce antibodies that are immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography. Antibodies against polypeptides of the present invention may also be employed to treat diseases of the invention, amongst others.

Polypeptides and polynucleotides of the present invention may also be used as vaccines. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a mammal may also be induced by a method comprises delivering a polypeptide of the present invention via a vector directing expression of the polynucleotide and coding for the polypeptide in vivo in order to induce such an immunological response to produce antibody to protect said animal from diseases of the invention. One way of administering the vector is by accelerating it into the desired cells as a coating on particles or otherwise. Such nucleic acid vector may comprise DNA, RNA, a modified nucleic acid, or a DNA/RNA hybrid. For use a vaccine, a polypeptide or a nucleic acid vector will be normally provided as a vaccine formulation (composition). The formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions that may contain anti-oxidants, buffers, bacteriostats and solutes that render the formulation instonic with the blood of the recipient; and aqueous and non-aqueous sterile suspensions that may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention have one or more biological functions that are of relevance in one or more disease states, in particular the diseases of the invention hereinbefore mentioned. It is therefore useful to identify compounds that stimulate or inhibit the function or level of the polypeptide. Accordingly, in a further aspect, the present invention provides for a method of screening compounds to identify those that stimulate or inhibit the function or level of the polypeptide. Such methods identify agonists or antagonists that may be employed for therapeutic and prophylactic purposes for such diseases of the invention as hereinbefore mentioned. Compounds may be identified from a variety of sources, for example, cells, cell-free preparations, chemical libraries, collections of chemical compounds, and natural product mixtures, Such agonists or antagonists so-identified may be natural or modified substrates, ligands, receptors, enzymes, etc., as the case may be, of the polypeptide; a structural or functional mimetic thereof (see Coligan et al., Current Protocols in Immunology 1(2):Chapter 5 (1991)) or a small molecule. Such small molecules preferably have a molecular weight below 2,000 daltons, more preferably between 300 and 1,000 daltons, and most preferably between 400 and 700 daltons. It is preferred that these small molecules are organic molecules.

The screening method may simply measure the binding of a candidate compound to the polypeptide, or to cells or membranes bearing the polypeptide, or a fusion protein thereof, by means of a label directly or indirectly associated with the candidate compound. Alternatively, the screening method may involve measuring or detecting (qualitatively or quantitatively) the competitive binding of a candidate compound to the polypeptide against a labeled competitor (e.g. agonist or antagonist). Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Further, the screening methods may simply comprise the steps of mixing a candidate compound with a solution containing a polypeptide of the present invention, to form a mixture, measuring a *GENE NAME activity in the mixture, and comparing the *GENE NAME activity of the mixture to a control mixture which contains no candidate compound.

Polypeptides of the present invention may be employed in conventional low capacity screening methods and also in high-throughput screening (HTS) formats. Such HTS formats include not only the well-estabiished use of 96- and, more recently, 384-well micotiter plates but also emerging methods such as the nanowell method described by Schullek et al, Anal Biochem., 246, 20–29, (1997).

Fusion proteins, such as those made from Fc portion and *GENE NAME polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

Screening Techniques

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents that may inhibit or enhance the production of polypeptide (also called antagonist or agonist, respectively) from suitably manipulated cells or tissues.

A polypeptide of the present invention may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}I$), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide that compete with the binding of the polypeptide to its receptors, if any. Standard methods for conducting such assays are well understood in the art.

Examples of antagonists of polypeptides of the present invention include antibodies or, in some cases, oligonucleotides or proteins that are closely related to the ligands, substrates, receptors, enzymes, etc., as the case may be, of the polypeptide, e.g., a fragment of the ligands, substrates, receptors, enzymes, etc.; or a small molecule that bind to the polypeptide of the present invention but do not elicit a response, so that the activity of the polypeptide is prevented.

Screening methods may also involve the use of transgenic technology and *GENE NAME gene. The art of constructing transgenic animals is well established. For example, the *GENE NAME gene may be introduced through microinjection into the male pronucleus of fertilized oocytes, retroviral transfer into pre- or post-implantation embryos, or injection of genetically modified, such as by electroporation, embryonic stem cells into host blastocysts. Particularly useful transgenic animals are so-called "knock-in" animals in which an animal gene is replaced by the human equivalent within the genome of that animal. Knock-in transgenic animals are useful in the drug discovery process, for target validation, where the compound is specific for the human target. Other useful transgenic animals are so-called "knock-out" animals in which the expression of the animal ortholog of a polypeptide of the present invention and encoded by an endogenous DNA sequence in a cell is partially or completely annulled. The gene knock-out may be targeted to specific cells or tissues, may occur only in certain cells or tissues as a consequence of the limitations of the technology, or may occur in all, or substantially all, cells in the animal. Transgenic animal technology also offers a whole animal expression-cloning system in which introduced genes are expressed to give large amounts of polypeptides of the present invention Screening kits for use in the above described methods form a further aspect of the present invention. Such screening kits comprise:
  (a) a polypeptide of the present invention;
  (b) a recombinant cell expressing a polypeptide of the present inventi
  (c) a cell membrane expressing a polypeptide of the present invention
  (d) an antibody to a polypeptide of the present invention;
  which polypeptide is preferably that of SEQ ID NO:2.

It will be appreciated that in any such kit, (a), (b), (c) or (d) may comprise a substantial component.

Glossary

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide" generally refers to any polyribonucleotide (RNA) or polydeoxribonucleotide (DNA), which may be unmodified or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any polypeptide comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques that are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, New York, 1993; Wold, F., Post-translational Protein Modifications: Perspectives and Prospects, 1–12, in Post-translational Covalent Modification of Proteins, B. C. Johnson, Ed., Academic Press, New York, 1983; Seifter et al., "Analysis for protein modifications and nonprotein cofactors", Meth Enzymol, 182, 626–646, 1990, and Rattan et al., "Protein Synthesis: Post-translational Modifications and Aging", Ann NY Acad Sci, 663, 48–62, 1992).

"Fragment" of a polypeptide sequence refers to a polypeptide sequence that is shorter than the reference sequence but that retains essentially the same biological function or activity as the reference polypeptide. "Fragment" of a polynucleotide sequence refers to a polynucleotide sequence that is shorter than the reference sequence of SEQ ID NO:1.

"Variant" refers to a polynucleotide or polypeptide that differs from a reference polynucleotide or polypeptide, but retains the essential properties thereof. A typical variant of a polynucleotide differs in nucleotide sequence from the reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from the reference polypeptide. Generally, alterations are limited so that the sequences of the reference polypeptide and the variant are closely similar overall and, in many regions, identical. A variant and reference polypeptide may differ in amino acid sequence by one or more substitutions, insertions, deletions in any combination. A substituted or inserted amino acid residue may or may not be one encoded by the genetic code. Typical conservative substitutions include Gly, Ala; Val, Ile, Leu; Asp, Glu; Asn, Gln; Ser, Thr; Lys, Arg; and Phe and Tyr. A variant of a polynucleotide or polypeptide may be naturally occurring such as an allele, or it may be a variant that is not known to occur naturally. Non-naturally occurring variants of polynucleotides and polypeptides may be made by mutagenesis techniques or by direct synthesis. Also included as variants are polypeptides having one or more post-translational modifications, for instance glycosylation, phosphorylation, methylation, ADP ribosylation and the like. Embodiments include methylation of the N-terminal amino acid, phosphorylations of serines and threonines and modification of C-terminal glycines.

"Allele" refers to one of two or more alternative forms of a gene occurring at a given locus in the genome.

"Polymorphism" refers to a variation in nucleotide sequence (and encoded polypeptide sequence, if relevant) at a given position in the genome within a population.

"Single Nucleotide Polymorphism" (SNP) refers to the occurrence of nucleotide variability at a single nucleotide position in the genome, within a population. An SNP may occur within a gene or within intergenic regions of the genome. SNPs can be assayed using Allele Specific Amplification (ASA). For the process at least 3 primers are required. A common primer is used in reverse complement to the polymorphism being assayed. This common primer can be between 50 and 1500 bps from the polymorphic base. The other two (or more) primers are identical to each other except that the final 3' base wobbles to match one of the two (or more) alleles that make up the polymorphism. Two (or more) PCR reactions are then conducted on sample DNA, each using the common primer and one of the Allele Specific Primers.

"Splice Variant" as used herein refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of that may encode different amino acid sequences. The term splice variant also refers to the proteins encoded by the above cDNA molecules.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectively, over the length of the sequences being compared.

"% Identity"—For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

"Similarity" is a further, more sophisticated measure of the relationship between two polypeptide sequences. In general, "similarity" means a comparison between the amino acids of two polypeptide chains, on a residue by residue basis, taking into account not only exact correspondences between a between pairs of residues, one from each of the sequences being compared (as for identity) but also, where there is not an exact correspondence, whether, on an evolutionary basis, one residue is a likely substitute for the other. This likelihood has an associated "score" from which the "% similarity" of the two sequences can then be determined.

Methods for comparing the identity and similarity of two or more sequences are well known in the art. Thus for instance, programs available in the Wisconsin Sequence Analysis Package, version 9.1 (Devereux J et al, Nucleic Acids Res, 12, 387–395, 1984, available from Genetics Computer Group, Madison, Wis., USA), for example the programs BESTFIT and GAP, may be used to determine the % identity between two polynucleotides and the % identity and the % similarity between two polypeptide sequences. BESTFIT uses the "local homology" algorithm of Smith and Waterman (J Mol Biol, 147, 195–197, 1981, Advances in Applied Mathematics, 2, 482–489, 1981) and finds the best single region of similarity between two sequences. BEST-FIT is more suited to comparing two polynucleotide or two polypeptide sequences that are dissimilar in length, the program assuming that the shorter sequence represents a portion of the longer. In comparison, GAP aligns two sequences, finding a "maximum similarity", according to the algorithm of Neddleman and Wunsch (J Mol Biol, 48, 443–453, 1970). GAP is more suited to comparing sequences that are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul S F et al, J Mol Biol, 215, 403–410, 1990, Altschul S F et al, Nucleic Acids Res., 25:389–3402, 1997, available from the National Center for Biotechnology Information (NCBI), Bethesda, Md., USA and accessible through the home page of the NCBI at www.ncbi.nlm.nih.gov) and FASTA (Pearson W R, Methods in Enzymology, 183, 63–99, 1990; Pearson W R and Lipman D J, Proc Nat Acad Sci USA, 85, 2444–2448, 1988, available as part of the Wisconsin Sequence Analysis Package).

Preferably, the BLOSUM62 amino acid substitution matrix (Henikoff S and Henikoff J G, Proc. Nat. Acad Sci. USA, 89, 10915–10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a reference polynucleotide or a polypeptide sequence, the query and the reference sequence being optimally aligned and the parameters of the program set at the default value, as hereinbefore described.

"Identity Index" is a measure of sequence relatedness which may be used to compare a candidate sequence (polynucleotide or polypeptide) and a reference sequence. Thus, for instance, a candidate polynucleotide sequence having, for example, an Identity Index of 0.95 compared to a reference polynucleotide sequence is identical to the reference sequence except that the candidate polynucleotide sequence may include on average up to five differences per each 100 nucleotides of the reference sequence. Such differences are selected from the group consisting of at least one nucleotide deletion, substitution, including transition and transversion, or insertion. These differences may occur at the 5' or 3' terminal positions of the reference polynucleotide sequence or anywhere between these terminal positions, interspersed either individually among the nucleotides in the reference sequence or in one or more contiguous groups within the reference sequence. In other words, to obtain a polynucleotide sequence having an Identity Index of 0.95 compared to a reference polynucleotide sequence, an average of up to 5 in every 100 of the nucleotides of the in the reference sequence may be deleted, substituted or inserted, or any combination thereof, as hereinbefore described. The same applies *mutatis mutandis* for other values of the Identity Index, for instance 0.96, 0.97, 0.98 and 0.99.

Similarly, for a polypeptide, a candidate polypeptide sequence having, for example, an Identity Index of 0.95 compared to a reference polypeptide sequence is identical to the reference sequence except that the polypeptide sequence may include an average of up to five differences per each 100 amino acids of the reference sequence. Such differences are selected from the group consisting of at least one amino acid deletion, substitution, including conservative and non-conservative substitution, or insertion. These differences may occur at the amino- or carboxy-terminal positions of the reference polypeptide sequence or anywhere between these terminal positions, interspersed either individually among the amino acids in the reference sequence or in one or more contiguous groups within the reference sequence. In other words, to obtain a polypeptide sequence having an Identity Index of 0.95 compared to a reference polypeptide sequence, an average of up to 5 in every 100 of the amino acids in the reference sequence may be deleted, substituted or inserted, or any combination thereof, as hereinbefore described. The same applies *mutatis mutandis* for other values of the Identity Index, for instance 0.96, 0.97, 0.98 and 0.99.

The relationship between the number of nucleotide or amino acid differences and the Identity Index may be expressed in the following equation:

$$n_a \leq x_a - (x_a \cdot I),$$

in which:
  $n_a$ is the number of nucleotide or amino acid differences,
  $x_a$ is the total number of nucleotides or amino acids in SEQ ID NO:1 or SEQ ID NO:2, respectively,
  I is the Identity Index,
  · is the symbol for the multiplication operator, and
  in which any non-integer product of $x_a$ and I is rounded down to the nearest integer prior to subtracting it from $x_a$.

"Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Ortholog" refers to a polynucleotide or polypeptide that is the functional equivalent of the polynucleotide or polypeptide in another species. "Paralog" refers to a polynucleotideor polypeptide that within the same species which is functionally similar.

"Fusion protein" refers to a protein encoded by two, unrelated, fused genes or fragments thereof. Examples have been disclosed in U.S. Pat. Nos. 5,541,087, 5,726,044. In the case of Fc-SIP-1 ligand, employing an immunoglobulin Fc region as a part of a fusion protein is advantageous for performing the functional expression of Fc-SIP-1 ligand or fragments of the ligand, to improve pharmacokinetic properties of such a fusion protein when used for therapy and to generate a dimeric SIP-1 ligand. The Fc-SIP-1 ligand DNA construct comprises in 5' to 3' direction, a secretion cassette, i.e. a signal sequence that triggers export from a mammalian cell, DNA encoding an immunoglobulin Fc region fragment, as a fusion partner, and a DNA encoding SIP-1 ligand or fragments thereof. In some uses it would be desirable to be able to alter the intrinsic functional properties (complement binding, Fc-Receptor binding) by mutating the functional Fc sides while leaving the rest of the fusion protein untouched or delete the Fc part completely after expression.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

DISCRIPTION OF FIGURES

FIG. 1

Interaction of *Survivin* with SIP-1 in *S. cerevisiae* EGY48/pSH18–32: *S. cerevisiae* EGY48/18–32 (Clontech) was transformed using plasmids encoding LexA- and Gal4-activation domain fusion proteins. Single colonies were isolated and streaked onto Media lacking Histidine, Tryptophane and Uracil (-WHU) and onto Medium lacking Histidine, Tryptophane, Leucine and Uracil containing 40 mg/l X-Gal (-WHLU-XGal). Growth of all strains on -WHU-Medium indicates presence of plasmids. Blue colour of yeast and growth on Medium lacking Leucine indicates interacion of baits and preys since expression of reporter-genes depends on a Two-Hybrid selection scheme. Lanes 1 and 2 are used as unspecific controls. Lane 3 indicates the specific interaction of *Survivin* and SIP-1 in this Yeast-Two-Hybrid System.

FIG. 2

SIP-1 Northern blot: Random primed $^{32}$P-radiolabelled SIP-1 probe was used for hybridisation consisting of 590 pase pairs corresponding to position 553–1143 of the SIP-1 cds. The blot was loaded with 2μg Poly (A) RNA per lane (Blot from Invitrogen: "real human tumor panel blot 3# D3803–50).

A 2.8 kb SIP-1 mRNA is detected in mRNA-samples of kidney normal tissue, kidney tumor tissue, lung normal tissue and lung tumor tissue

FIG. 3

Multiplex PCR of mRNA derived from human HeLa cells using the "Gene Specific Relative RT-PCR Kit" (Protocol according to producer of this kit system: Ambion):

Human HeLa cells were cell phase arrested using the following treatment (G1-Phase: L-Mimosine [400 μM]; S-Phase: Thymidine [2 mM]; G2/M Phase: Nocodazole [40 ng/ml]). The cell cycle status was controlled by FACS analysis; control cells were treated with 1 μl DMSO/ml medium. SIP-1 mRNA expression appears to be upregulated during S-phase and G2/M phase of the cell cycle

FIG. 4

SIP-1/*Survivin* coimmunoprecipitation: SIP-1 and *Survivin* interact in human HeLa cells and after expression as in vitro translated proteins. Analysis of the SIP-1/*Survivin* Interaction via V5-antibody mediated Immunoprecipitation (IP) Assays

FURTHER EXAMPLES

Plasmid Constructs

Cloning of pDBLeu—*survivin*: The *survivin* gene was cloned from cDNA of human PC-3 cells by using gene specific PCR primer pairs with in-built restriction sites for NheI and StuI, amplifying the coding sequence of *survivin*. The PCR product was cloned via TA-cloning into the pCRII vector (Invitrogen). The insert was isolated via NheI/StuI restriction and cloned into the Y2H vector pDBLeu (PROQUEST™ Two-Hybrid System, GibcoBRL LIFE TECHNOLOGIES) creating pDBLeu-*Survivin*. This results in generation of a fusion gene construct for the expression of the Gal4 DB domain fused to the full length *survivin* peptid. All vectors were confirmed by sequencing.

PCR primers for the cloning of the *survivin* gene were the following:
  NheI-5' *survivin* primer: Primer 1
  StuI-3' *survivin* primer: Primer 2

Selection of *Survivin* Interacting Proteins

A yeast Two Hybrid screen (Proquest, Life Technologies) using pDBLeu-*Survivin* as the bait construct was performed using a human HeLa cell cDNA-Y2H-library and a cDNA library derived from human fetal brain tissue (selection was performed on -Trp, -Leu, -His Minimalmedium containing 25 mM 3-Aminotriazole). SIP-1 clones were isolated from both libraries. Interaction was confirmed by β-Galactosidase-filter assay and Uracile, Tryptophane and Leucine lacking medium as described in the manufacturers protocoll.

One positive clone was isolated and sequenced. The corresponding interacting protein ligand was termed SIP-1 (*Survivin*-lnteracting-Protein-1) ligand and the sequences have been disclosed in SEQ ID NO: 1 and NO: 2

What is claimed is:

1. An isolated human polypeptide selected from the group consisting of:
   (a) a polypeptide encoded by a polynucleotide comprising the sequence of SEQ ID NO:1;
   (b) a polypeptide comprising a polypeptide sequence comprising at least 95% identity along the entire length of the polypeptide sequence of SEQ ID NO:2 and which is encoded for by a polynucleotide sequence which hybridizes to the comvlement of SEQ ID NO:1 under stringent conditions comprising overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1×SSC at 65° C., and which polypeptide binds to *survivin;*
   (c) a polypeptide comprising at least 95% identity along the entire length of the polypeptide sequence of SEQ ID NO:2 and which is encoded for by a polynucleotide sequence which hybridizes to the complement of SEQ ID NO:1 under stringent conditions comprising overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1×SSC at 65° C., and which polypeptide binds to *survivin;* and
   (d) the polypeptide sequence of SEQ ID NO:2.

2. An isolated polypeptide comprising the polypeptide sequence of SEQ ID NO:2.

3. The polypeptide of claim 2 which is the polypeptide sequence of SEQ ID NO:2.

4. An isolated human polynucleotide selected from the group consisting of:
   (a) a polynucleotide comprising a polynucleotide sequence comprising at least 95% identity along the entire length of the polynucleotide sequence of SEQ ID NO:1 which hybridizes to the complement of SEQ ID NO:1 under stringent conditions comprising overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA; followed by washing the filters in 0.1×SSC at 65° C.;

(b) a polynucleotide comprising at least 95% identity along the entire length of the polynucleotide of SEQ ID NO:1 which hybridizes to the complement of SEQ ID NO:1 under stringent conditions comprising overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1×SSC at 65° C. and which binds to *survivin;*

(c) a polynucleotide comprising a polynucleotide sequence encoding a polypeptide sequence comprising at least 95% identity along the entire length of the polypeptide sequence of SEQ ID NO:2 and which hybridizes to the complement of SEQ ID NO:1 under stringent conditions comprising overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1×SSC at 65° C., and which polypeptide binds to *survivin;*

(d) a polynucleotide comprising a polynucleotide sequence encoding a polypeptide sequence comprising at least 95% identity along the entire length of the polypeptide sequence of SEQ ID NO:2 and which hybridizes to the complement of SEQ ID NO:1 under stringent conditions comprising overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1×SSC at 65° C., and which polypeptide binds to *survivin;*

(e) a polynucleotide which is the RNA equivalent of a polynucleotide of (a) to (d); and (f) a polynucleotide sequence complementary over its entire length to said polynucleotide of any one of (a) to (e).

5. A polynucleotide of claim 4 selected from the group consisting of:

(a) a polynucleotide comprising the polynucleotide of SEQ ID NO:1;

(b) the polynucleotide of SEQ ID NO:1;

(c) a polynucleotide comprising a polynucleotide sequence encoding the polypeptide of SEQ ID NO:2; and (d) a polynucleotide encoding the polypeptide of SEQ ID NO:2.

6. An expression vector comprising a polynucleotide capable of producing a polypeptide of claim 1 when said expression vector is present in a compatible host cell.

7. A recombinant host cell comprising the expression vector of claim 6, wherein said cell is expressing a polypeptide of claim 1.

8. A process for producing a polypeptide, comprising culturing a host cell as defined in claim 7 under conditions sufficient for the production of said polypeptide and recovering the polypeptide from the culture medium.

9. A fusion protein comprising an Immunoglobulin Fc-region and a polypeptide of claim 1.

10. An isolated antibody which is immunospecific for the polypeptide of claim 1.

11. A method for screening to identify compounds that stimulate or inhibit the *survivin* binding activity of the polypeptide of claim 1, or its expression in cells, comprising a method selected from the group consisting of:

(a) measuring or, detecting, quantitatively or qualitatively, the binding of a candidate compound to the polypeptide, or a fusion protein thereof, by means of a label directly or indirectly associated with the candidate compound;

(b) measuring the competition of binding of a candidate compound to the polypeptide or a fusion protein thereof, in the presence of a labeled competitor;

(c) testing whether a candidate compound results in a signal generated by activation or inhibition of the polypeptide, using detection systems appropriate to the cells or cell membranes expressing the polypeptide;

(d) mixing a candidate compound with a solution containing a polypeptide of claim 1, to form a mixture, measuring activity of the polypeptide in the mixture, and comparing the activity of the mixture to a control mixture which contains no candidate compound; or (e) detecting the effect of a candidate compound on the production of mRNA encoding said polypeptide or said polypeptide in cells, using an ELISA assay.

12. The polypeptide of claim 1, comprising at least 99% identity.

13. The polynucleotide of claim 4, comprising at least 99% identity.

* * * * *

UNITED STATES PATENT AND TRADEMARK OFFICE
CERTIFICATE OF CORRECTION

PATENT NO.         : 7,166,701 B2  
APPLICATION NO. : 10/239391  
DATED                  : January 23, 2007  
INVENTOR(S)        : Bernd Hentsch It is certified that error appears in the above-identified patent and that said Letters Patent is hereby corrected as shown below:

On Front Page, Foreign Application Priority Data reads "001064088" should read -- 00106408.8 --  
Column 31, line 19, reads "which binds" should read -- which polypeptide binds --  
Column 32, line 28 reads "measuring or, detecting" should read -- measuring or detecting --

Signed and Sealed this

Eleventh Day of December, 2007

JON W. DUDAS  
*Director of the United States Patent and Trademark Office*

SEQUENCE LISTING

<160> NUMBER OF SEQ ID NOS: 4

<210> SEQ ID NO 1
<211> LENGTH: 3263
<212> TYPE: DNA
<213> ORGANISM: Homo sapiens
<220> FEATURE:
<221> NAME/KEY: CDS
<222> LOCATION: (233)..(2320)
<220> FEATURE:
<221> NAME/KEY: modified_base
<222> LOCATION: (103)
<223> OTHER INFORMATION: n = a, t, c, g, unknown or other
<220> FEATURE:
<221> NAME/KEY: modified_base
<222> LOCATION: (107)
<223> OTHER INFORMATION: n = a, t, c, g, unknown or other
<220> FEATURE:
<221> NAME/KEY: modified_base
<222> LOCATION: (120)
<223> OTHER INFORMATION: n = a, t, c, g, unknown or other
<220> FEATURE:
<221> NAME/KEY: modified_base
<222> LOCATION: (3063)
<223> OTHER INFORMATION: n = a, t, c, g, unknown or other
<220> FEATURE:
<221> NAME/KEY: modified_base
<222> LOCATION: (3076)
<223> OTHER INFORMATION: n = a, t, c, g, unknown or other
<220> FEATURE:
<221> NAME/KEY: modified_base
<222> LOCATION: (3203)
<223> OTHER INFORMATION: n = a, t, c, g, unknown or other
<220> FEATURE:
<221> NAME/KEY: modified_base
<222> LOCATION: (3210)
<223> OTHER INFORMATION: n = a, t, c, g, unknown or other
<220> FEATURE:
<221> NAME/KEY: modified_base
<222> LOCATION: (3227)
<223> OTHER INFORMATION: n = a, t, c, g, unknown or other
<220> FEATURE:
<221> NAME/KEY: modified_base
<222> LOCATION: (3250)
<223> OTHER INFORMATION: n = a, t, c, g, unknown or other
<220> FEATURE:
<221> NAME/KEY: modified_base
<222> LOCATION: (3256)
<223> OTHER INFORMATION: n = a, t, c, g, unknown or other

<400> SEQUENCE: 1

```
tgacgcacgg aggggccggg acgcgatttg ccgcgagtga ctggagccgc aaccgtcgcc      60
gctgctgccg ccgccgcccg ggcccgctcc gcccccagcc cgncttnctc ccgccgcgcn     120
ctccgcctcc gcccgcaatt cggctacagt tcccctgtct tccccaacgc cccggagccg     180
ccggccgcta gcgtcagcgc cagccagaat taaggaagtt cactggagta aa atg gag    238
                                                           Met Glu
                                                             1 gcc tca gta ata tta ccc att ctg aag aaa aaa cta gcc ttc ctt tca      286
Ala Ser Val Ile Leu Pro Ile Leu Lys Lys Lys Leu Ala Phe Leu Ser
      5                  10                  15 gga gga aag gac aga cgg agt ggc ctc att ttg aca att cca tta tgc     334
```

|     |     |     |     |     |     |     |     |     |     |     |     |     |     |     |     |
|---|---|---|---|---|---|---|---|---|---|---|---|---|---|---|---|
| Gly | Gly | Lys | Asp | Arg | Arg | Ser | Gly | Leu | Ile | Leu | Thr | Ile | Pro | Leu | Cys |
|     | 20  |     |     |     |     | 25  |     |     |     | 30  |     |     |     |     |     |

```
ctc gaa cag aca aat atg gat gag ctg agt gtc acc tta gac tac cta      382
Leu Glu Gln Thr Asn Met Asp Glu Leu Ser Val Thr Leu Asp Tyr Leu
 35              40                  45                  50 ctc agc att cca agt gag aag tgt aag gct aga gga ttt acc gtg att      430
Leu Ser Ile Pro Ser Glu Lys Cys Lys Ala Arg Gly Phe Thr Val Ile
             55                  60                  65 gtg gat ggc aga aaa tca cag tgg aat gtg gtg aaa aca gta gtc gta      478
Val Asp Gly Arg Lys Ser Gln Trp Asn Val Val Lys Thr Val Val Val
         70                  75                  80 atg cta cag aat gtt gtt cca gct gag gtg tcc ctt gtt tgt gtg gta      526
Met Leu Gln Asn Val Val Pro Ala Glu Val Ser Leu Val Cys Val Val
     85                  90                  95 aag cca gat gaa ttc tgg gat aag aaa gta acg cat ttt tgt ttt tgg     574
Lys Pro Asp Glu Phe Trp Asp Lys Lys Val Thr His Phe Cys Phe Trp
 100                 105                 110 aag gag aag gat aga ctt ggc ttt gag gtt att tta gtg tcc gcc aac     622
Lys Glu Lys Asp Arg Leu Gly Phe Glu Val Ile Leu Val Ser Ala Asn
115                 120                 125                 130 aaa ttg act cgt tat ata gaa cca tgc caa tta aca gaa gat ttt ggt     670
Lys Leu Thr Arg Tyr Ile Glu Pro Cys Gln Leu Thr Glu Asp Phe Gly
             135                 140                 145 ggg agt ctc acc tat gat cac atg gac tgg tta aat aag agg ctg gtt     718
Gly Ser Leu Thr Tyr Asp His Met Asp Trp Leu Asn Lys Arg Leu Val
         150                 155                 160 ttt gag aag ttt aca aag gaa tct aca tca tta tta gat gaa ctt gct     766
Phe Glu Lys Phe Thr Lys Glu Ser Thr Ser Leu Leu Asp Glu Leu Ala
     165                 170                 175 ttg att aac aat gga agt gat aaa gga aat cag caa gag aaa gaa agg     814
Leu Ile Asn Asn Gly Ser Asp Lys Gly Asn Gln Gln Glu Lys Glu Arg
 180                 185                 190 tct gtg gat tta aac ttt ctt cca tcg gtt gat cct gaa aca gtt ctt     862
Ser Val Asp Leu Asn Phe Leu Pro Ser Val Asp Pro Glu Thr Val Leu
195                 200                 205                 210 cag aca ggg cat gaa ttg ttg tcc gaa tta cag cag cgt cga ttt aat     910
Gln Thr Gly His Glu Leu Leu Ser Glu Leu Gln Gln Arg Arg Phe Asn
             215                 220                 225 ggc tca gac gga ggg gtt tca tgg tct cct atg gat gat gaa ctt ctt     958
Gly Ser Asp Gly Gly Val Ser Trp Ser Pro Met Asp Asp Glu Leu Leu
         230                 235                 240 gca cag cca cag gtt atg aaa tta tta gat tca ctc cga gag caa tat    1006
Ala Gln Pro Gln Val Met Lys Leu Leu Asp Ser Leu Arg Glu Gln Tyr
     245                 250                 255 acc cgc tac cag gaa gtt tgt agg caa cgt agc aag cgc aca cag tta    1054
Thr Arg Tyr Gln Glu Val Cys Arg Gln Arg Ser Lys Arg Thr Gln Leu
 260                 265                 270 gaa gag att caa cag aag gta atg cag gtg gtg aac tgg cta gaa ggg    1102
Glu Glu Ile Gln Gln Lys Val Met Gln Val Val Asn Trp Leu Glu Gly
275                 280                 285                 290 cct gga tca gaa caa cta aga gcc cag tgg ggc att gga gac tcc att    1150
Pro Gly Ser Glu Gln Leu Arg Ala Gln Trp Gly Ile Gly Asp Ser Ile
             295                 300                 305 agg gcc tcc cag gcc cta cag cag aaa cac gaa gag att gag agc cag    1198
Arg Ala Ser Gln Ala Leu Gln Gln Lys His Glu Glu Ile Glu Ser Gln
         310                 315                 320 cac agt gaa tgg ttt gca gtg tat gtg gaa ctt aat cag caa att gca    1246
His Ser Glu Trp Phe Ala Val Tyr Val Glu Leu Asn Gln Gln Ile Ala
     325                 330                 335
```

```
gca ctc ttg aat gct ggc gat gag gaa gat ctt gtg gaa cta aag tca      1294
Ala Leu Leu Asn Ala Gly Asp Glu Glu Asp Leu Val Glu Leu Lys Ser
340                 345                 350 ctg cag caa caa ctt agt gat gtt tgt tat cga cag gcc agt cag ctg      1342
Leu Gln Gln Gln Leu Ser Asp Val Cys Tyr Arg Gln Ala Ser Gln Leu
355                 360                 365                 370 gaa ttt agg caa aat ctc tta caa gca gct ctt gaa ttt cat ggk gtt      1390
Glu Phe Arg Gln Asn Leu Leu Gln Ala Ala Leu Glu Phe His Gly Val
            375                 380                 385 gcc caa gat ttg tct cag cag ttg gat ggc tta tta ggg atg ttg tgc      1438
Ala Gln Asp Leu Ser Gln Gln Leu Asp Gly Leu Leu Gly Met Leu Cys
        390                 395                 400 gta gat gta gca cca gct gat gga gca tcg att cag caa act tta aaa      1486
Val Asp Val Ala Pro Ala Asp Gly Ala Ser Ile Gln Gln Thr Leu Lys
    405                 410                 415 ctg ctt gaa gag aag ctg aaa agt gtt gat gtg gga ttg caa ggt ttg      1534
Leu Leu Glu Glu Lys Leu Lys Ser Val Asp Val Gly Leu Gln Gly Leu
420                 425                 430 cgt gaa aaa ggt caa ggt ctc ctg gat cag atc tcc aat cag gca tcc      1582
Arg Glu Lys Gly Gln Gly Leu Leu Asp Gln Ile Ser Asn Gln Ala Ser
435                 440                 445                 450 tgg gcc tat gga aag gat gta acc att gaa aat aaa gaa aat gtg gac      1630
Trp Ala Tyr Gly Lys Asp Val Thr Ile Glu Asn Lys Glu Asn Val Asp
            455                 460                 465 cac ata caa gga gtg atg gaa gat atg cag ctt aga aaa caa aga tgt      1678
His Ile Gln Gly Val Met Glu Asp Met Gln Leu Arg Lys Gln Arg Cys
        470                 475                 480 gaa gac atg gta gat gtg cga agg tta aag atg ctt cag atg gtg cag      1726
Glu Asp Met Val Asp Val Arg Arg Leu Lys Met Leu Gln Met Val Gln
    485                 490                 495 ttg ttt aaa tgt gaa gaa gat gct gcc cag gca gta gaa tgg cta agt      1774
Leu Phe Lys Cys Glu Glu Asp Ala Ala Gln Ala Val Glu Trp Leu Ser
500                 505                 510 gaa ctt ctg gat gct ctg ctt aag act cac atc aga ttg ggc gat gat      1822
Glu Leu Leu Asp Ala Leu Leu Lys Thr His Ile Arg Leu Gly Asp Asp
515                 520                 525                 530 gct caa gaa acg aaa gtt ttg ctg gaa aag cat aga aaa ttt gtt gat      1870
Ala Gln Glu Thr Lys Val Leu Leu Glu Lys His Arg Lys Phe Val Asp
            535                 540                 545 gtt gca cag agc act tat gac tat ggc agg cag ttg cta cag gcc aca      1918
Val Ala Gln Ser Thr Tyr Asp Tyr Gly Arg Gln Leu Leu Gln Ala Thr
        550                 555                 560 gtt gtg tta tgc caa tct ttg cgc tgc act tct cgg tca tct ggg gat      1966
Val Val Leu Cys Gln Ser Leu Arg Cys Thr Ser Arg Ser Ser Gly Asp
    565                 570                 575 aca ctt cct cga ctg aac aga gta tgg aaa caa ttt aca ata gca tct      2014
Thr Leu Pro Arg Leu Asn Arg Val Trp Lys Gln Phe Thr Ile Ala Ser
580                 585                 590 gaa gag aga gta cat aga ttg gaa atg gct att gca ttt cac tca aat      2062
Glu Glu Arg Val His Arg Leu Glu Met Ala Ile Ala Phe His Ser Asn
595                 600                 605                 610 gct gaa aag att ttg cag gac tgt cca gaa gag cct gaa gct att aat      2110
Ala Glu Lys Ile Leu Gln Asp Cys Pro Glu Glu Pro Glu Ala Ile Asn
            615                 620                 625 gat gag gag caa ttt gat gaa att gaa gca gtt ggg aaa tca ctt ttg      2158
Asp Glu Glu Gln Phe Asp Glu Ile Glu Ala Val Gly Lys Ser Leu Leu
        630                 635                 640 gat aga tta act gtt cca gta gtt tat cct gat gga acc gaa caa tat      2206
Asp Arg Leu Thr Val Pro Val Val Tyr Pro Asp Gly Thr Glu Gln Tyr
    645                 650                 655
```

```
ttt ggg agt cca agt gac atg gct tct act gca gaa aac atc aga gac    2254
Phe Gly Ser Pro Ser Asp Met Ala Ser Thr Ala Glu Asn Ile Arg Asp
660                 665                 670 agg atg aaa cta gtt aat ctc aaa agg cag cag ctg aga cat cct gaa    2302
Arg Met Lys Leu Val Asn Leu Lys Arg Gln Gln Leu Arg His Pro Glu
675                 680                 685                 690 atg gtg acc aca gag agc taatagctac cagctaccta cagatttgca           2350
Met Val Thr Thr Glu Ser
                695 gttcataatc ccgcatgttg tcaacatact acagcattag ccaccacacc ttaagatgca   2410 tttcacagcc aaaataagtc tcatttcttt tcatgacaca tttctcttta catgttaaca   2470 ccttgctact accaaggcat aattacttaa catgcttcga ggctgtagat tccaagtatc   2530 ttaaaagaag gaactataaa cattgcactg aaaacttgct ttaaagcttt acctgacctg   2590 tcagtttgta gacaaacaac tgataataag ctttgaatgg tgctaataag agtaggaatt   2650 ctctctatta aaagaaaaa aaaagttgc ccttcctcca caggtgattt agtaaattta    2710 gacagtagtt aaactcttgt tagtagacag tggtgtcctc aaaattttac tttgtaattc   2770 ttcagaattg attattttta ttgtgtcaat acagagaaag cctttcagat ctttgatata   2830 tcatagtcat taaagaccct tttcctattt gtattgataa tgtattaaaa gttgtttgtg   2890 cttaataaaa gacttcttta aacatcttat ttaatttagt agttacatcc tatttccaaa   2950 catgagtgcc ttatttaaaa gggcattctt aggactgtga ggatggttta atatttgttt   3010 ttcatggtgg ttgcatgtat tttagacagg aaatacatat gtaagcatgt gtntataata   3070 aataancatg ttttatcatg aaaaaattat tgtgaacaat ttaaatcttt aagaacttat   3130 taataatgga atactattct aattttcctc ttttccactt gaaaatttcc caaattatta   3190 acttcccccaa aanatttgtn tttaggggaa gaaggtnaag aaaagggttc ttattcctcn   3250 tgttanccctt aat                                                     3263

<210> SEQ ID NO 2
<211> LENGTH: 696
<212> TYPE: PRT
<213> ORGANISM: Homo sapiens

<400> SEQUENCE: 2

Met Glu Ala Ser Val Ile Leu Pro Ile Leu Lys Lys Leu Ala Phe
1               5                   10                  15

Leu Ser Gly Gly Lys Asp Arg Arg Ser Gly Leu Ile Leu Thr Ile Pro
                20                  25                  30

Leu Cys Leu Glu Gln Thr Asn Met Asp Glu Leu Ser Val Thr Leu Asp
            35                  40                  45

Tyr Leu Leu Ser Ile Pro Ser Glu Lys Cys Lys Ala Arg Gly Phe Thr
        50                  55                  60

Val Ile Val Asp Gly Arg Lys Ser Gln Trp Asn Val Lys Thr Val
65                  70                  75                  80

Val Val Met Leu Gln Asn Val Pro Ala Glu Val Ser Leu Val Cys
                85                  90                  95

Val Val Lys Pro Asp Glu Phe Trp Asp Lys Val Thr His Phe Cys
            100                 105                 110

Phe Trp Lys Glu Lys Asp Arg Leu Gly Phe Glu Val Ile Leu Val Ser
        115                 120                 125

Ala Asn Lys Leu Thr Arg Tyr Ile Glu Pro Cys Gln Leu Thr Glu Asp
    130                 135                 140
```

-continued

```
Phe Gly Gly Ser Leu Thr Tyr Asp His Met Asp Trp Leu Asn Lys Arg
145                 150                 155                 160

Leu Val Phe Glu Lys Phe Thr Lys Glu Ser Thr Ser Leu Leu Asp Glu
                165                 170                 175

Leu Ala Leu Ile Asn Asn Gly Ser Asp Lys Gly Asn Gln Gln Glu Lys
                180                 185                 190

Glu Arg Ser Val Asp Leu Asn Phe Leu Pro Ser Val Asp Pro Glu Thr
                195                 200                 205

Val Leu Gln Thr Gly His Glu Leu Leu Ser Glu Leu Gln Gln Arg Arg
            210                 215                 220

Phe Asn Gly Ser Asp Gly Gly Val Ser Trp Ser Pro Met Asp Asp Glu
225                 230                 235                 240

Leu Leu Ala Gln Pro Gln Val Met Lys Leu Leu Asp Ser Leu Arg Glu
                245                 250                 255

Gln Tyr Thr Arg Tyr Gln Glu Val Cys Arg Gln Arg Ser Lys Arg Thr
                260                 265                 270

Gln Leu Glu Glu Ile Gln Gln Lys Val Met Gln Val Val Asn Trp Leu
            275                 280                 285

Glu Gly Pro Gly Ser Glu Gln Leu Arg Ala Gln Trp Gly Ile Gly Asp
290                 295                 300

Ser Ile Arg Ala Ser Gln Ala Leu Gln Gln Lys His Glu Glu Ile Glu
305                 310                 315                 320

Ser Gln His Ser Glu Trp Phe Ala Val Tyr Val Glu Leu Asn Gln Gln
                325                 330                 335

Ile Ala Ala Leu Leu Asn Ala Gly Asp Glu Glu Asp Leu Val Glu Leu
                340                 345                 350

Lys Ser Leu Gln Gln Gln Leu Ser Asp Val Cys Tyr Arg Gln Ala Ser
            355                 360                 365

Gln Leu Glu Phe Arg Gln Asn Leu Leu Gln Ala Ala Leu Glu Phe His
            370                 375                 380

Gly Val Ala Gln Asp Leu Ser Gln Gln Leu Asp Gly Leu Leu Gly Met
385                 390                 395                 400

Leu Cys Val Asp Val Ala Pro Ala Asp Gly Ala Ser Ile Gln Gln Thr
                405                 410                 415

Leu Lys Leu Leu Glu Glu Lys Leu Lys Ser Val Asp Val Gly Leu Gln
                420                 425                 430

Gly Leu Arg Glu Lys Gly Gln Gly Leu Leu Asp Gln Ile Ser Asn Gln
            435                 440                 445

Ala Ser Trp Ala Tyr Gly Lys Asp Val Thr Ile Glu Asn Lys Glu Asn
450                 455                 460

Val Asp His Ile Gln Gly Val Met Glu Asp Met Gln Leu Arg Lys Gln
465                 470                 475                 480

Arg Cys Glu Asp Met Val Asp Val Arg Arg Leu Lys Met Leu Gln Met
                485                 490                 495

Val Gln Leu Phe Lys Cys Glu Glu Asp Ala Ala Gln Ala Val Glu Trp
                500                 505                 510

Leu Ser Glu Leu Leu Asp Ala Leu Leu Lys Thr His Ile Arg Leu Gly
            515                 520                 525

Asp Asp Ala Gln Glu Thr Lys Val Leu Glu Lys His Arg Lys Phe
            530                 535                 540

Val Asp Val Ala Gln Ser Thr Tyr Asp Tyr Gly Arg Gln Leu Leu Gln
545                 550                 555                 560
```

```
Ala Thr Val Val Leu Cys Gln Ser Leu Arg Cys Thr Ser Arg Ser Ser
                565                 570                 575

Gly Asp Thr Leu Pro Arg Leu Asn Arg Val Trp Lys Gln Phe Thr Ile
                580                 585                 590

Ala Ser Glu Glu Arg Val His Arg Leu Glu Met Ala Ile Ala Phe His
            595                 600                 605

Ser Asn Ala Glu Lys Ile Leu Gln Asp Cys Pro Glu Glu Pro Glu Ala
            610                 615                 620

Ile Asn Asp Glu Glu Gln Phe Asp Glu Ile Glu Ala Val Gly Lys Ser
625                 630                 635                 640

Leu Leu Asp Arg Leu Thr Val Pro Val Val Tyr Pro Asp Gly Thr Glu
                645                 650                 655

Gln Tyr Phe Gly Ser Pro Ser Asp Met Ala Ser Thr Ala Glu Asn Ile
                660                 665                 670

Arg Asp Arg Met Lys Leu Val Asn Leu Lys Arg Gln Gln Leu Arg His
                675                 680                 685

Pro Glu Met Val Thr Thr Glu Ser
            690                 695

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Primer 1
      (Nhel-5' survivin primer)

<400> SEQUENCE: 3
ctagctagca tgggtgcccc gacgttg                                        27

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Primer 2
      (Stul-3' survivin primer)

<400> SEQUENCE: 4
taggccttca atccatggca gccag                                          25
```